United States Patent [19]
Yamamoto et al.

[11] Patent Number: 6,071,392
[45] Date of Patent: Jun. 6, 2000

[54] CHOLESTEROL SENSOR

[75] Inventors: Tomohiro Yamamoto; Toshihiko Yoshioka; Shiro Nankai, all of Hirakata, Japan

[73] Assignee: Matsushita Electric Industrial Co., Ltd., Osaka, Japan

[21] Appl. No.: 09/089,350

[22] Filed: Jun. 3, 1998

[30] Foreign Application Priority Data

Jun. 3, 1997 [JP] Japan ................................ 9-145303

[51] Int. Cl.[7] .................................................. G01N 27/26
[52] U.S. Cl. ........................................... 204/403; 435/817
[58] Field of Search ............................. 204/403; 435/817

[56] References Cited

U.S. PATENT DOCUMENTS

| | | | |
|---|---|---|---|
| 5,312,590 | 5/1994 | Gunashingham | 422/56 |
| 5,695,947 | 12/1997 | Guo et al. | 435/11 |

FOREIGN PATENT DOCUMENTS

| | | |
|---|---|---|
| 0230786 | 12/1986 | European Pat. Off. |
| 0771867 | 4/1996 | European Pat. Off. |
| 0794429 | 3/1997 | European Pat. Off. |
| 0849589 | 11/1997 | European Pat. Off. |
| 63-109799 | 5/1988 | Japan |
| 2-62952 | 3/1990 | Japan |
| 2145815 | 4/1985 | United Kingdom |

*Primary Examiner*—T. Tung
*Assistant Examiner*—Alex Noguerola
*Attorney, Agent, or Firm*—McDermott, Will & Emery

[57] ABSTRACT

A cholesterol sensor is disclosed which comprises an electrode system having a measuring electrode and a counter electrode formed on an electrically insulating base plate, an electrode coating layer for covering the electrode system and a reaction reagent layer formed on or in the vicinity of the electrode coating layer, wherein the reaction reagent layer comprises at least an enzyme for catalyzing cholesterol oxidation, an enzyme having a cholesterol ester hydrolyzing activity and a surfactant, the electrode coating layer comprises at least one selected from the group consisting of water-soluble cellulose derivatives and saccharides and is contained at such a concentration that imparts sufficient viscosity to a sample solution for enabling it to hinder invasion of said surfactant into said electrode system when said electrode coating layer is dissolved in said sample solution supplied to said sensor. This configuration best eliminates impairment of sensor response due to electrode degeneration caused by invading surfactant into the electrode system.

12 Claims, 8 Drawing Sheets

Concentration of the standard cholesterol solution

Concentration of the standard cholesterol solution

CHOLESTEROL SENSOR

BACKGROUND OF THE INVENTION

The present invention relates to a cholesterol sensor enabling rapid and high accuracy quantification of cholesterol and cholesterol ester contained in a sample in a simplified manner.

A biosensor has been proposed in the Japanese Laid-Open Patent Publication Hei 2-062952 as a system for simplified quantification of a specific component in a sample without diluting or agitating a sample solution.

This prior art biosensor is completed by first forming an electrode system comprising a measuring electrode, a counter electrode and a reference electrode on an electrically insulating base plate by using a screen printing method or the like, and then forming an enzyme reaction layer comprising a hydrophilic polymer, oxidoreductase, an electron acceptor, and additionally a buffer, if occasion demands, in close proximity to the previously formed electrode system.

Upon dropping a sample solution containing a substrate on the enzyme reaction layer, dissolution of the layer takes place, which in turn triggers reaction between the enzyme and the substrate, causing a reduction of the electron acceptor. Upon completion of the enzyme reaction, the reduced electron acceptor is oxidized electrochemically. The concentration of the substrate in the sample can be determined by reading the oxidation current that flows upon electrochemical oxidation of the electron acceptor.

This biosensor can be used for measurements of various materials if an appropriate enzyme corresponding to the substrate of a target material is selected.

The use of cholesterol oxidase or cholesterol dehydrogenase as the oxidoreductase can yield a biosensor for measurement of serum cholesterol.

Serum cholesterol level which serves as diagnostic standard at various medical institutions is a sum of serum cholesterol and cholesterol ester concentrations.

As is known, cholesterol ester can not serve as a substrate for oxidation by cholesterol oxidase. Therefore, in order to determine serum cholesterol concentrations as diagnostic standard, an additional step of converting cholesterol ester into cholesterol becomes necessary. Cholesterol esterase is a known enzyme for catalyzing this step.

However, since cholesterol ester in sera is encapsulated in one kind of pseudomicelle lipoprotein, the probability of contact of this substance with the enzyme cholesterol esterase becomes low, which greatly prolongs conversion of cholesterol ester into cholesterol. It has been widely accepted that addition of an optimal surfactant can improve the probability of contact of cholesterol ester with cholesterol esterase, thereby increasing the catalytic activity of cholesterol esterase. For example, the Japanese Unexamined Patent Publication Hei 6-71440 proposes a structure of a cholesterol sensor for measuring cholesterol by coloring reaction where an enzyme having a cholesterol ester hydrolyzing activity coexists with a surfactant alkylphenoxy-polyglycidol in the same layer.

However, inclusion of a surfactant in the biosensor having the structure as disclosed in the Japanese Laid-Open Patent Publication Sho 63-139242 or Hei 2-062952 results in marked inaccuracy of the sensor response probably due to the structure of the employed electrode system. In other words, the biosensor has a working electrode and a counter electrode whose surfaces are formed by printing a carbon paste. Whereas, the underlying layers and the leads of those electrodes are formed by printing a silver paste in order to improve their electric conductivity. When a sample solution dissolving a surfactant is brought into contact with the electrode system of this configuration, the surfactant invades the carbon layer to touch the silver leads of the underlying layer. In such a structure, the silver leads participate in the electrochemical reaction upon application of a potential onto the electrodes at the time of measurement of the responsive current value of the sensor, which sometimes causes an increase in the current value. This means that the resultant responsive current value of the sensor does not reflect exact cholesterol concentrations in the sample. Moreover, invasion of the surfactant into the carbon electrodes sometimes lowers electrode activity, i.e., electron conduction velocity in the electrode/liquid interface, which is considered to impair the response characteristic of the sensor.

BRIEF SUMMARY OF THE INVENTION

In view of the drawbacks of the prior art cholesterol sensors, the primary object of the present invention is to provide a cholesterol sensor facilitating rapid measurement of the cholesterol concentration in a sample by best decreasing the effect of a surfactant on the electrode system.

The present invention provides a cholesterol sensor comprising an electrically insulating base plate, an electrode system having a measuring electrode and a counter electrode formed on the base plate, an electrode coating layer for covering the electrode system and a reaction reagent layer formed on or in the vicinity of the electrode coating layer, wherein the reaction reagent layer comprises at least an enzyme for catalyzing cholesterol oxidation (hereafter referred to as "cholesterol oxidation catalyst"), an enzyme having a cholesterol ester hydrolyzing activity (hereafter referred to as "cholesterol ester hydrolyzing enzyme") and a surfactant, the electrode coating layer comprises at least one selected from the group consisting of water-soluble cellulose derivatives and saccharides and is contained at such a concentration that imparts sufficient viscosity to a sample solution for enabling it to hinder invasion of said surfactant into said electrode system when said electrode coating layer is dissolved in said sample solution supplied to said sensor.

In another aspect, the present invention provides a cholesterol sensor further comprising a cover member which is integrated into the base plate so as to form a sample supply path for supplying a sample solution to the electrode system between the cover member and the base plate, wherein the reaction reagent layer is located somewhere in the sample supply path.

According to the present invention, even such an enzyme that requires a surfactant for expressing its enzyme activity exerts its inherent function effectively in a cholesterol sensor. This yields a cholesterol sensor permitting measurements in a shorter time than before. Accordingly, the cholesterol sensor in accordance with the present invention is useful for measurement of blood cholesterol levels.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
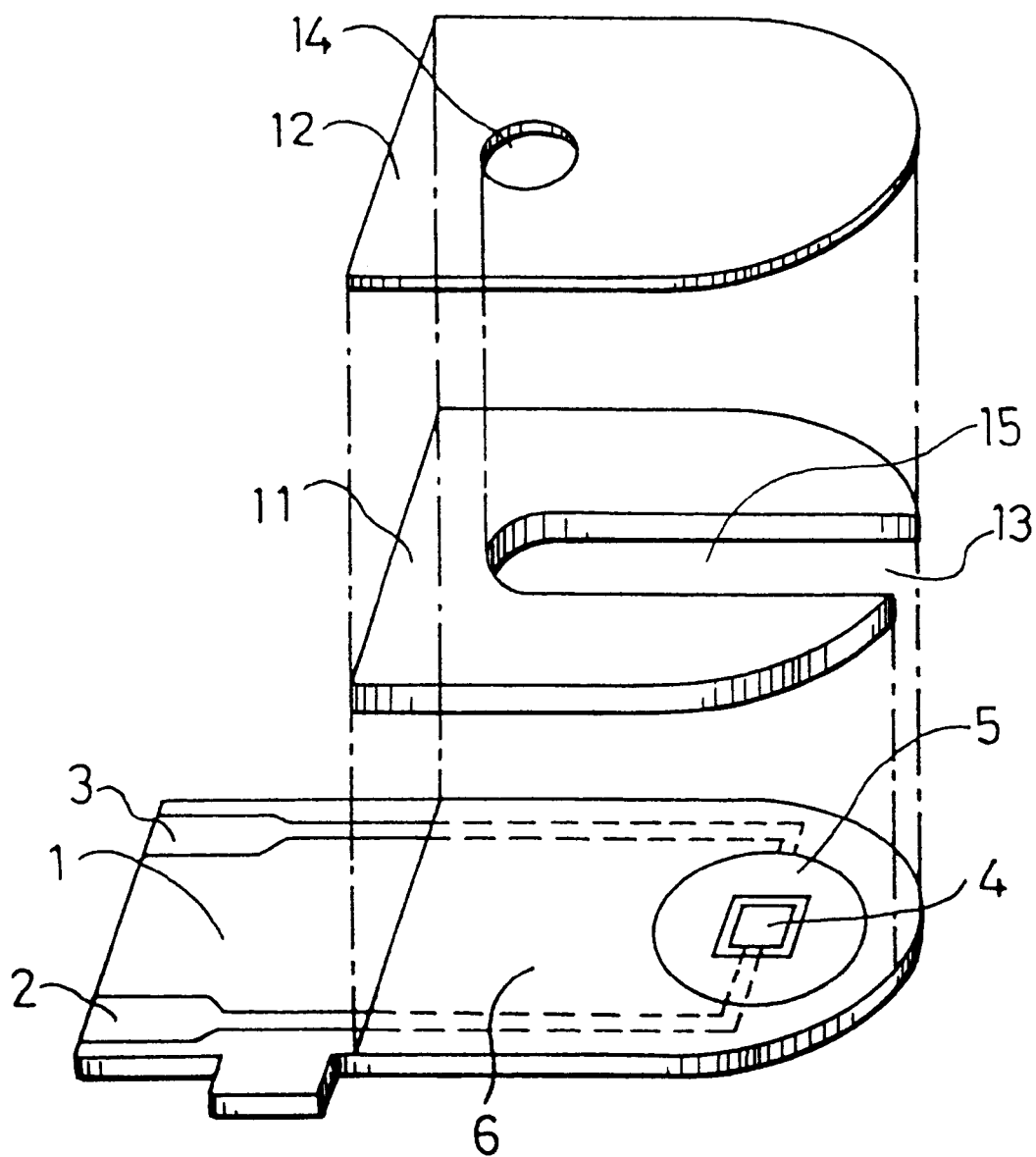
FIG. 1 is an exploded perspective view of a cholesterol sensor in accordance with one example of the present invention with an omission of an electrode coating layer and a reaction reagent layer.

The present invention is based on the inventors' discovery that surface coating of an electrode system with an adequate amount of water-soluble cellulose derivative and/or saccharide can alleviate the effect on the electrode system of a surfactant contained at such a concentration that is high enough to activate cholesterol ester hydrolyzing enzyme, for example, cholesterol esterase. As a result, a responsive current value precisely reflecting cholesterol concentration in a sample can be obtained. In other words, when a sample solution is supplied to a sensor, the sample solution dissolves not merely reaction reagents located on or in the vicinity of the electrode system but also water-soluble cellulose derivative and/or saccharide contained in an electrode coating layer for covering the electrode system. The water-soluble cellulose derivative and saccharide act to impart viscosity to the sample solution, hindering easy invasion of a surfactant into the electrode system. On the other hand, compared to surfactant, electron acceptors are movable even in a viscous aqueous solution. This feature of electron acceptors facilitates measurement of the results of enzyme reaction at the electrode system.

As stated above, in order to best hinder the movement of surfactant, it is appropriate in general that the water-soluble cellulose derivative and/or saccharide should cover the electrode system in a range of 0.4 to 2.5 mg/cm$^2$, more preferably in a range of 0.8 to 1.6 mg/cm$^2$ per unit area of the electrode system. It is preferred that the water-soluble cellulose derivative and/or saccharide should cover the entire surface of the electrode system.

The sensor in accordance with the present invention is directed particularly to quantification of blood cholesterol. Typical sensors in accordance with the present invention will be illustrated in the below-mentioned Examples. In the present experiments, about 3 $\mu$l of a sample solution is used per sensor chip. The electrode system has an area of about 10 mm$^2$. Appropriate amounts of cholesterol oxidation catalyst and cholesterol ester hydrolyzing enzyme which are carried on a sensor chip are 0.15 to 1.5 units and 1.5 to 6.0 units, respectively. For enhancing the activity of the latter, it is suited to contain the surfactant at 0.7×10$^{-2}$ to 1.0×10$^{-2}$ $\mu$g. For best eliminating the effect of the surfactant on the electrode system, the water-soluble cellulose derivative and/or saccharide should be contained 40 to 250 $\mu$g, more preferably 80 to 160 $\mu$g. On the basis of unit area of the electrode system, the values are 0.4 to 2.5 mg/cm$^2$ and 0.8 to 1.6 mg/cm$^2$. In addition, the concentrations of the cholesterol oxidation catalyst, the cholesterol ester hydrolyzing enzyme and the surfactant should be 50 to 500 units/ml, 500 to 2,000 units/ml and 0.25 to 1.0 wt %, respectively, in 3 $\mu$l of a sample solution.

A simple method for covering the surface of the electrode system with the water-soluble cellulose derivative and/or saccharide is to drop their aqueous solution on the electrode system, followed by drying. It is preferable to use a 0.5 to 2.0 wt % aqueous solution of cellulose derivative. If the concentration of water-soluble cellulose derivative is higher than this range, the resultant aqueous solution becomes too viscous, disturbing addition of an exact amount. Even if successful in forming a coating layer on the electrode system with such viscous aqueous solution, the formed layer is prone to fall off.

On the other hand, if the concentration of water-soluble cellulose derivative is lower than this range, it becomes necessary to increase the dropping amount of the resultant aqueous solution. Moreover, when dropped, the aqueous solution will be dispersed due to its low viscosity, which occasionally makes it impossible to carry required amounts of water-soluble cellulose derivative on the electrode system. However, an aqueous solution of the cellulose derivative below the above-specified range may be usable if only it is dropped in aliquot several times and dried.

Even when the saccharide is used alone, an electrode coating layer can be formed using an aqueous solution of saccharide at a concentration substantially equal to the aqueous solution of cellulose derivative. However, the electrode coating layer consisting of only saccharide is more prone to fall off as compared with the coating layer containing water-soluble cellulose derivative alone. It is therefore better to mix the both in forming the electrode coating layer, avoiding single use of saccharide.

It is preferable that the reaction reagents are carried at least in part on the electrode coating layer and that the reaction reagent layer contains a water-soluble cellulose derivative or a saccharide. The presence of water-soluble cellulose derivative or saccharide in the reaction reagent layer helps to alleviate the effect of the surfactant on the electrode system. Those two substances to be contained in the reaction reagent layer are preferably provided on the electrode coating layer, together with the cholesterol oxidation catalyst. Whereas, the cholesterol ester hydrolyzing enzyme and the surfactant are preferably provided on the upper side of the layer formed by the water-soluble cellulose derivative or saccharide and the cholesterol oxidation catalyst or on the cover member side so as to isolate them from the electrode coating layer.

In forming the reaction reagent layer comprising the water-soluble cellulose derivative or saccharide, it is better to drop a mixed aqueous solution of an enzyme with a water-soluble cellulose derivative or saccharide on the electrode coating layer, followed by drying. The concentration of water-soluble cellulose derivative or saccharide in the mixed aqueous solution is desirably 0.1 to 1.0 wt %. In this range of concentration, complete mixing of the electrode coating layer and the reaction reagent layer would not take place during sensor production. Concentrations above this range are not preferred, because they may hinder dispersion of the substrate and the electron acceptor, which in turn impairs the sensor response.

The reaction reagent layer may be formed into a multi-layer comprising a layer of cholesterol oxidation catalyst, a layer of surfactant, and a layer of cholesterol ester hydrolyzing enzyme. The surfactant and the cholesterol ester hydrolyzing enzyme may be mixed together to coexist in the same layer. A reaction reagent layer may be split into plural segments and provided at plural positions. Alternatively, it may be formed into several layers each having different reagents at plural positions. Those layers can be positioned at various sites in a sensor.

For example, they may be positioned at an exposed side of the cover member so as to form the sample supply path for supplying a sample solution to the sensor, or at an opening side of the sample supply path which is proximal to the electrode system. In either case, it is desired that the reaction reagent layer is readily dissolved in the sample solution introduced into the sensor.

As stated previously, the surfactant layer is preferably isolated from the electrode system so as to alleviate the adverse effect of the surfactant on the electrode system. This means that it is preferable to form the layer of the cholesterol ester hydrolyzing enzyme above the layer of oxidoreductase which exists above the electrode system and subsequently form the surfactant layer immediately above the oxidoreductase layer, at an exposed side of the cover member to the sample supply path, or parallel to the electrode system even if there is a risk of lowering the activity of the cholesterol ester hydrolyzing enzyme in some degree. Normal reaction reagent layer contains an electron acceptor.

In order to facilitate introduction of the sample solution into the reaction reagent layer, it is preferred to form a lipid layer so as to cover the layer formed above the electrode system.

Applicable cholesterol oxidation catalysts include cholesterol oxidase, cholesterol dehydrogenase, and its coenzyme nicotinamide adenine dinucleotide.

As the cholesterol ester hydrolyzing enzyme, cholesterol esterase and lipoprotein lipase may be used.

As the water-soluble cellulose derivative, carboxymethyl cellulose, ethylcellulose, and hydroxypropyl cellulose may be used.

As the saccharide, monosaccharide such as glucose, fructose, etc. and oligosaccharide such as trehalose, sucrose, lactose, maltose, etc. may be used.

Applicable surfactant may be selected from among n-octyl-β-D-thioglucoside, polyethylene glycol monododecylether, sodium cholate, dodecyl-β-maltoside, sucrose monolaurate, sodium deoxycholate, sodium taurodeoxycholate, N,N-bis(3-Dgluconamidopropyl) cholamide, N,N-bis(3-D-gluconamidopropyl) deoxycholamide and polyoxyethylene-p-t-octylphenylether and the like.

As the electron acceptor, ferricyanide ion, p-benzoquinone, phenazine methosulfate and ferrocene may be used. Other arbitrary water-soluble compounds that can mediate electron transfer between enzyme and electrodes may also be used.

As the lipid, amphipathic lipids such as phospholipids including lecithin, phosphatidylethanolamine, phosphatidylserine and the like are used preferably.

In measuring oxidation current values, although a two-electrode system comprising a measuring electrode and a counter electrode and a three-electrode system further comprising a reference electrode are applicable, the latter can give more accurate measurement results.

In the following, the present invention will be described more specifically, referring to concrete examples.

FIG. 1 is an exploded perspective view of a cholesterol sensor from which the electrode coating layer and the reaction reagent layer have been omitted.

Numeral 1 designates an electrically insulating base plate of polyethylene terephthalate. Above the base plate 1, leads 2 and 3, and the underlying layer of an electrode system are formed by printing a silver paste using a screen printing method. The base plate 1 is further formed thereon with the electrode system comprising a measuring electrode 4 and a counter electrode 5 by printing a conductive carbon paste containing a resin binder. An electrically insulating layer 6 is also formed on the base plate 1 by printing an insulating paste. The aim of the insulating layer 6 is to regulate the area of the exposed portions of the measuring electrode 4 and the counter electrode 5 to a constant level and to cover the leads 2 and 3 partially. The measuring electrode 4 is a square measuring 1 mm for one side. The counter electrode 5 which defines the size of the electrode system appears like a disc having an outer diameter of 3.6 mm.

The base plate 1 is bonded with a cover member composed of a cover 12 having an air vent 14 and a spacer 11 in a positional relationship as shown by the dotted chain line in FIG. 1, which completes a cholesterol sensor. The spacer 11 is provided with a slit 15 for forming a sample supply path between the base plate 1 and the cover 12. Numeral 13 corresponds to an opening of the sample supply path.

Figure 2:
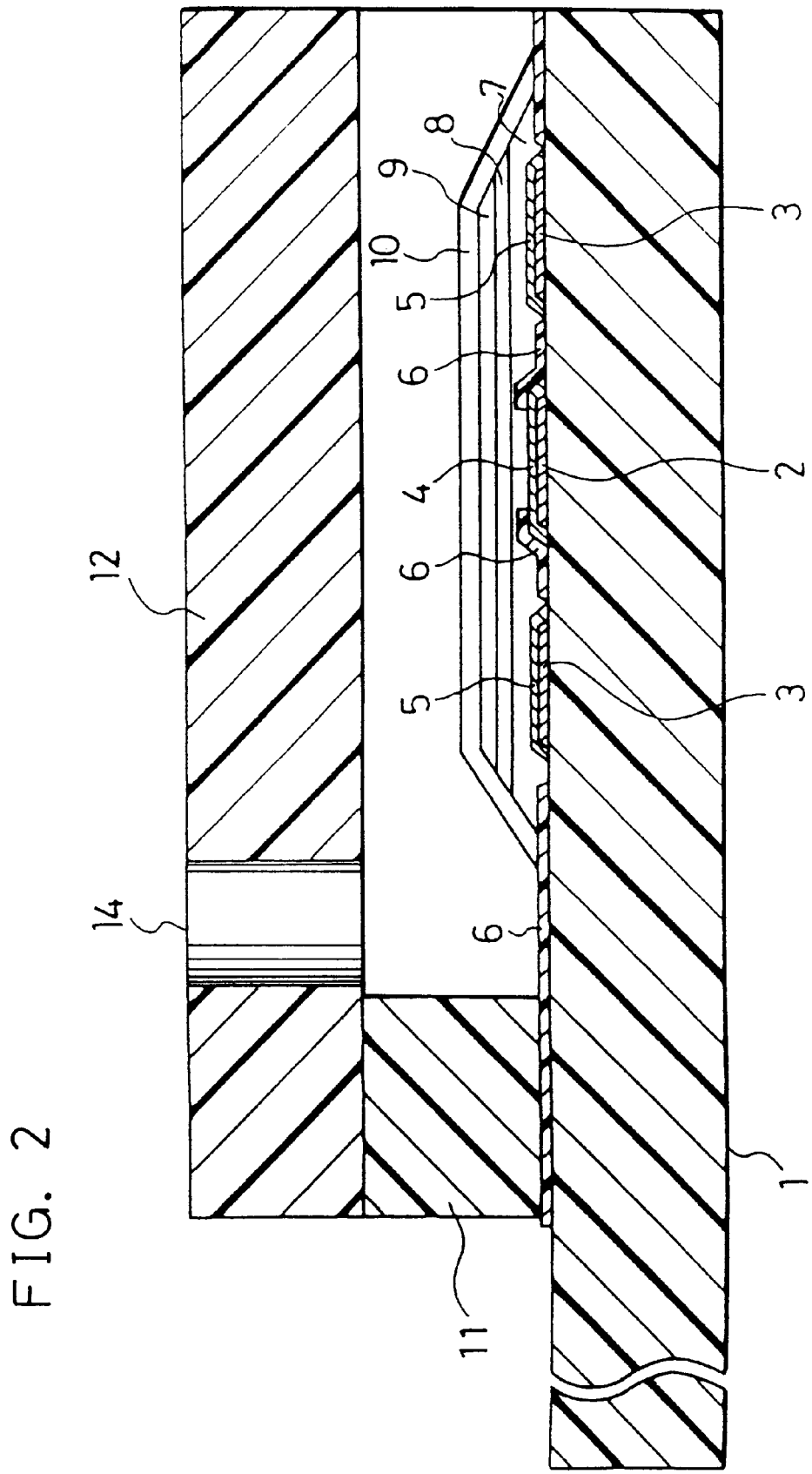
FIG. 2 is a longitudinal cross-sectional view showing the vital parts of the same cholesterol sensor.

FIG. 2 shows a longitudinal cross-sectional view of a cholesterol sensor in accordance with one example of the present invention. Similar to FIG. 1, after formed above the base plate 1, the electrode system is formed thereon with an electrode coating layer 7 of a water-soluble cellulose derivative or a saccharide, a layer 8 containing a cholesterol oxidation catalyst, an electron acceptor and a hydrophilic polymer, a layer 9 containing a cholesterol ester hydrolyzing enzyme and a surfactant, and a lipid layer 10.

Figure 3:
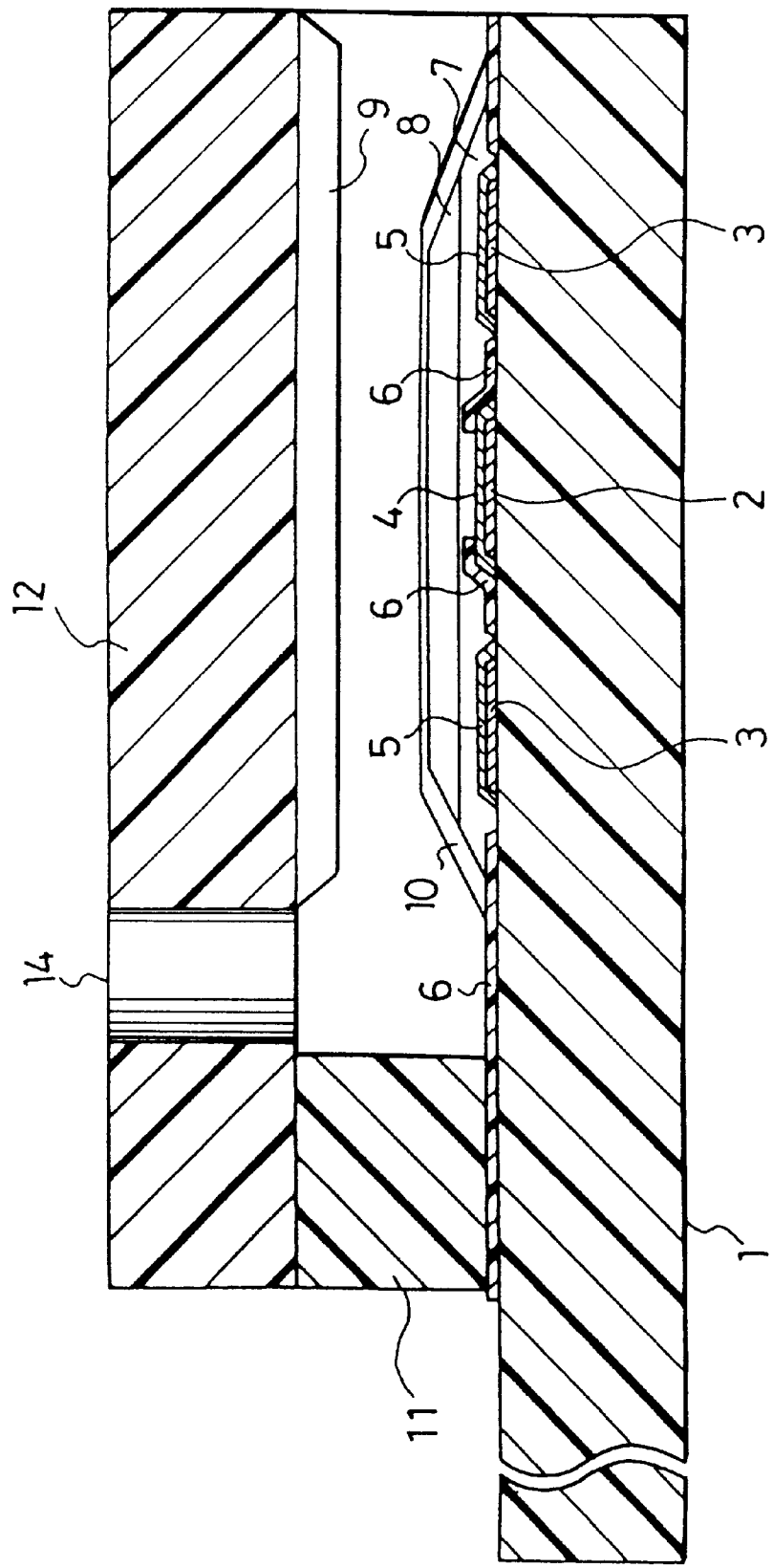
FIG. 3 is a longitudinal cross-sectional view showing the vital parts of a cholesterol sensor in accordance with another example of the present invention.

FIG. 3 shows a longitudinal cross-sectional view of a cholesterol sensor in accordance with another example of the present invention.

Similar to FIG. 2, the electrode system, the electrode coating layer 7 and the layer 8 containing a cholesterol oxidation catalyst, an electron acceptor and a hydrophilic polymer are formed. The layer 8 is then covered with the lipid layer 10. The layer 9 containing a cholesterol ester hydrolyzing enzyme and a surfactant is formed at an exposed side of the cover 12 to the sample supply path.

Figure 4:
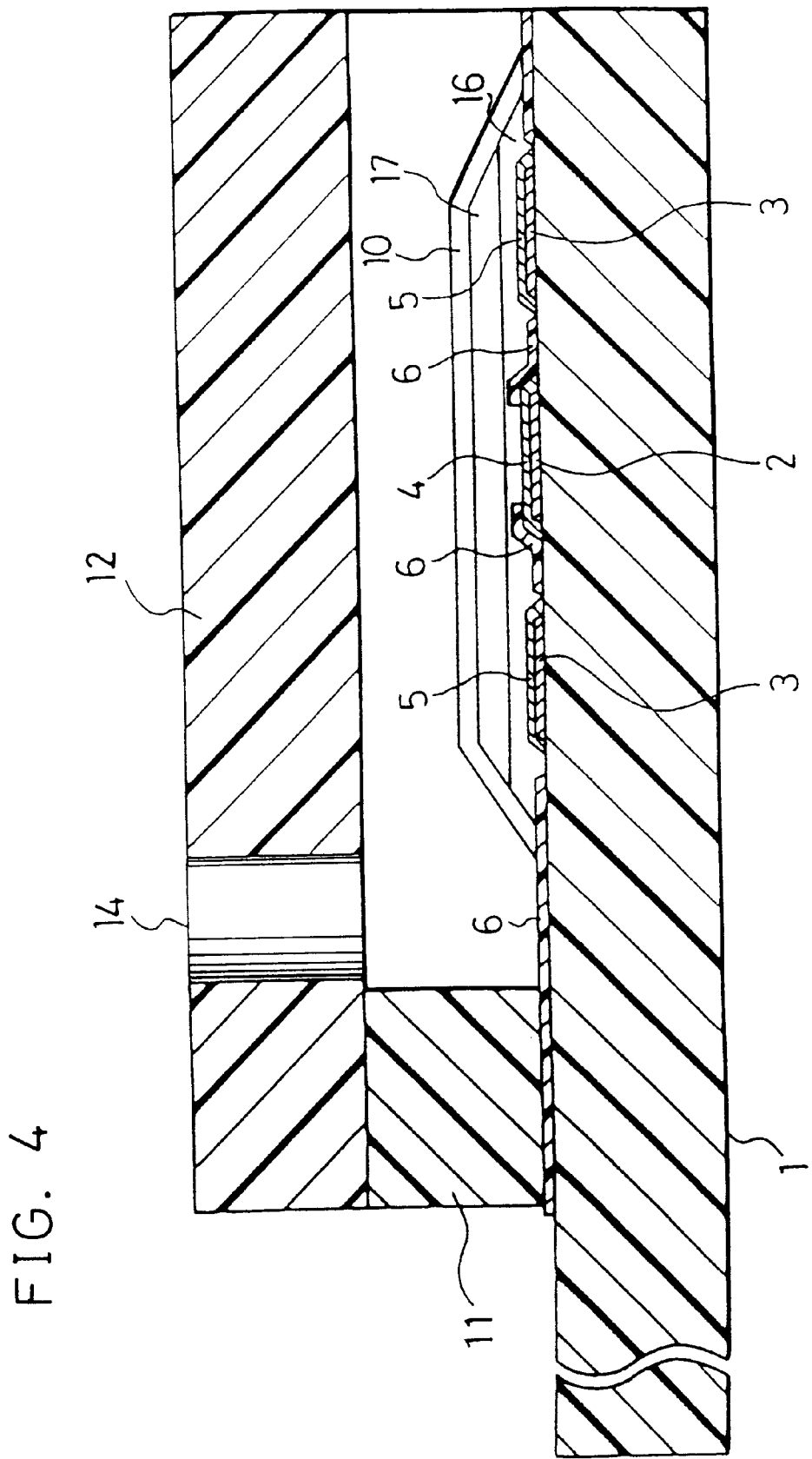
FIG. 4 is a longitudinal cross-sectional view showing the vital parts of a cholesterol sensor in accordance with still another example of the present invention.

FIG. 4 is a longitudinal cross-sectional view of a cholesterol sensor in accordance with still another example of the present invention.

Similar to FIG. 2, the electrode system is formed together with an electrode coating layer 16 comprising a water-soluble cellulose derivative and a saccharide. Above the layer 16, a layer 17 containing a cholesterol oxidation catalyst, an electron acceptor, a cholesterol ester hydrolyzing enzyme and a surfactant is formed. The layer 17 is then covered with the lipid layer 10.

Figure 5:
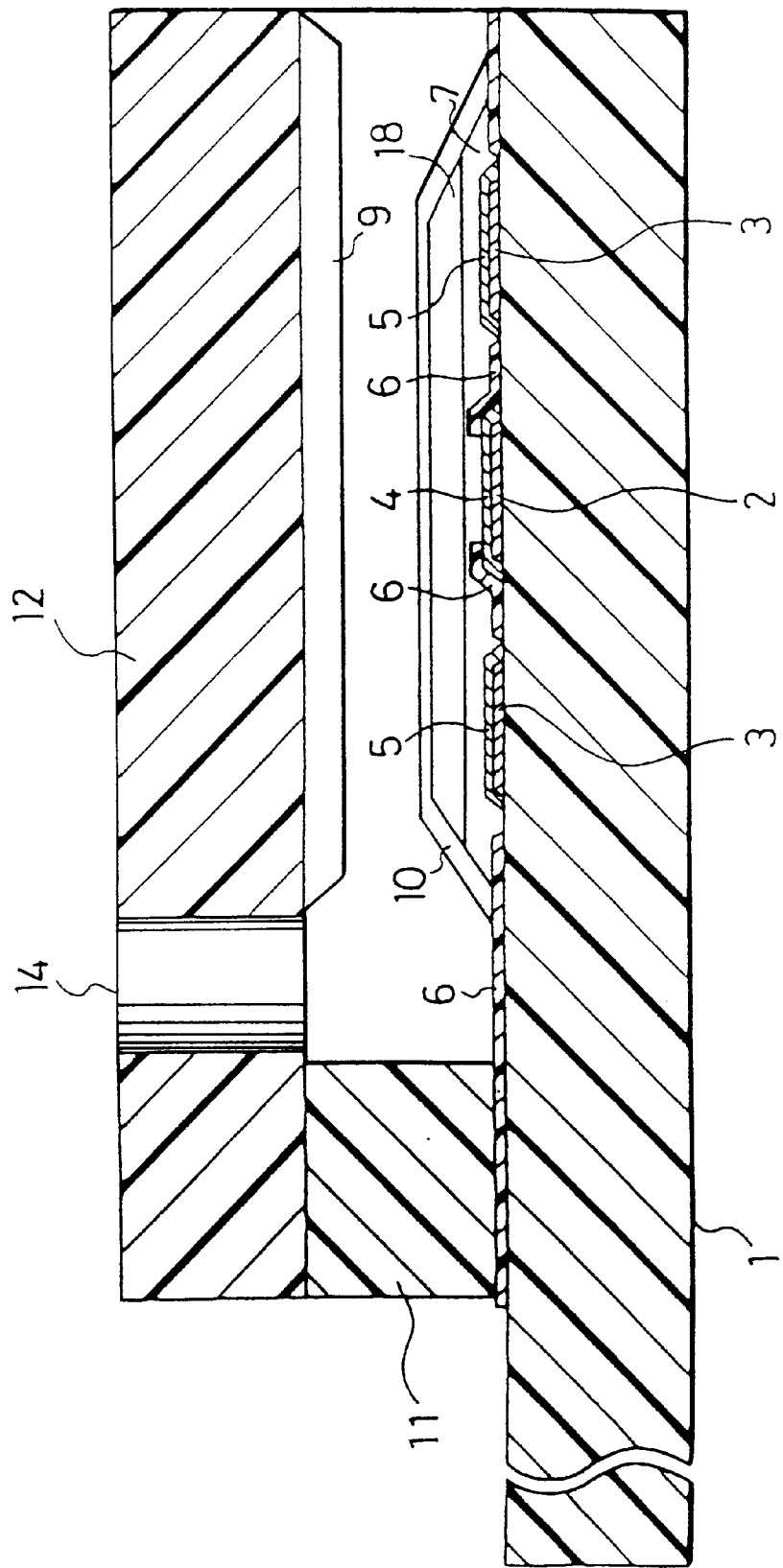
FIG. 5 is a longitudinal cross-sectional view showing the vital parts of a cholesterol sensor in accordance with a further example of the present invention.

FIG. 5 is a longitudinal cross-sectional view of a cholesterol sensor in accordance with a further example of the present invention.

Similar to FIG. 2, the electrode system is formed together with an electrode coating layer 7. Then, a layer 18 containing a cholesterol oxidation catalyst, an electron acceptor and a saccharide is further formed, which is then covered with the lipid layer 10. The layer 9 containing a cholesterol ester hydrolyzing enzyme and a surfactant is formed at an exposed side of the cover 12 to the sample supply solution.

EXAMPLE 1

After dropping 10 μl of a 1.5 wt % aqueous sodium solution of a hydrophilic polymer carboxymethyl cellulose (hereafter abbreviated to "CMC") above the electrode system formed on the base plate 1 shown in FIG. 1, the whole was dried in a hot drier at 50° C. for 10 min so as to form a CMC layer 7. Subsequently, a cholesterol oxidation catalyst Nocardia sp.-derived cholesterol oxidase (EC 1.1.3.6; hereafter abbreviated to "ChOD") and an electron acceptor potassium ferricyanide were mixed with a 0.25% aqueous solution of CMC to form a mixed aqueous solution A. Then, 5 μl of the solution A was dropped on the CMC layer 7 and dried in a hot drier at 50° C. for 10 min so as to form a ChOD-potassium ferricyanide-CMC layer 8. Furthermore, after preparation of a mixed aqueous solution B by mixing Pseudomonas sp.-derived cholesterol esterase (EC 3.1.1.13; hereafter abbreviated to "ChE") with a surfactant polyoxyethylene-p-t-octylphenylether (Triton X-100), 5 μl of the solution B was dropped on the previously formed ChOD-potassium ferricyanide-CMC layer 8 and dried in a hot drier at 50° C. for 10 min so as to form a ChE-surfactant layer 9. Triton X-100 is contained in the solution B at 0.25 wt %.

In the above-mentioned steps, transient swelling of the CMC layer 7 may occur due to its intake of water contained in the solution A when it is dropped on the CMC layer 7. During the subsequent drying step, a part of the CMC layer 7 is mixed with the enzyme and others in the solution A to form a mixed layer. However, because of the presence of CMC in the solution A, most of the CMC contained in the CMC layer 7 remains not mixed, causing only swelling. Moreover, since agitation is not performed after dropping, mixing of the CMC layer 7 with the solution A remains incomplete. Therefore, the surface of the electrode system can be covered with only CMC, which eliminates potential contact of the surface of the electrode system with the enzyme and electron acceptor. This configuration is considered to preclude adverse changes in the electrode system due to protein adsorption onto the surface of the electrode system and chemical action of those substances having an oxidizing ability, such as potassium ferricyanide. Furthermore, this structure also prevents the surfactant Triton X-100 contained in the solution B from arriving at the surface of the electrode system thereby eliminating degeneration of the electrode system.

Above the ChE-surfactant layer 9, 5 μl of a 0.5% toluene solution of phosphatidylcholine was dropped so as to cover the layer 9 and dried, which gave a lecithin layer 10. The presence of the lecithin layer 10 helps smooth introduction of the sample solution, but it is not essential for the enzyme reaction.

After formation of the reaction reagent layer comprising the CMC layer 7, ChOD-potassium ferricyanide-CMC layer 8, ChE-surfactant layer 9 and lecithin layer 10 in the above-mentioned manner, the cover 12 and the spacer 11 were bonded in a positional relationship shown by the dotted chain line in FIG. 1, which completed a cholesterol sensor having the structure of FIG. 2.

Figure 6:
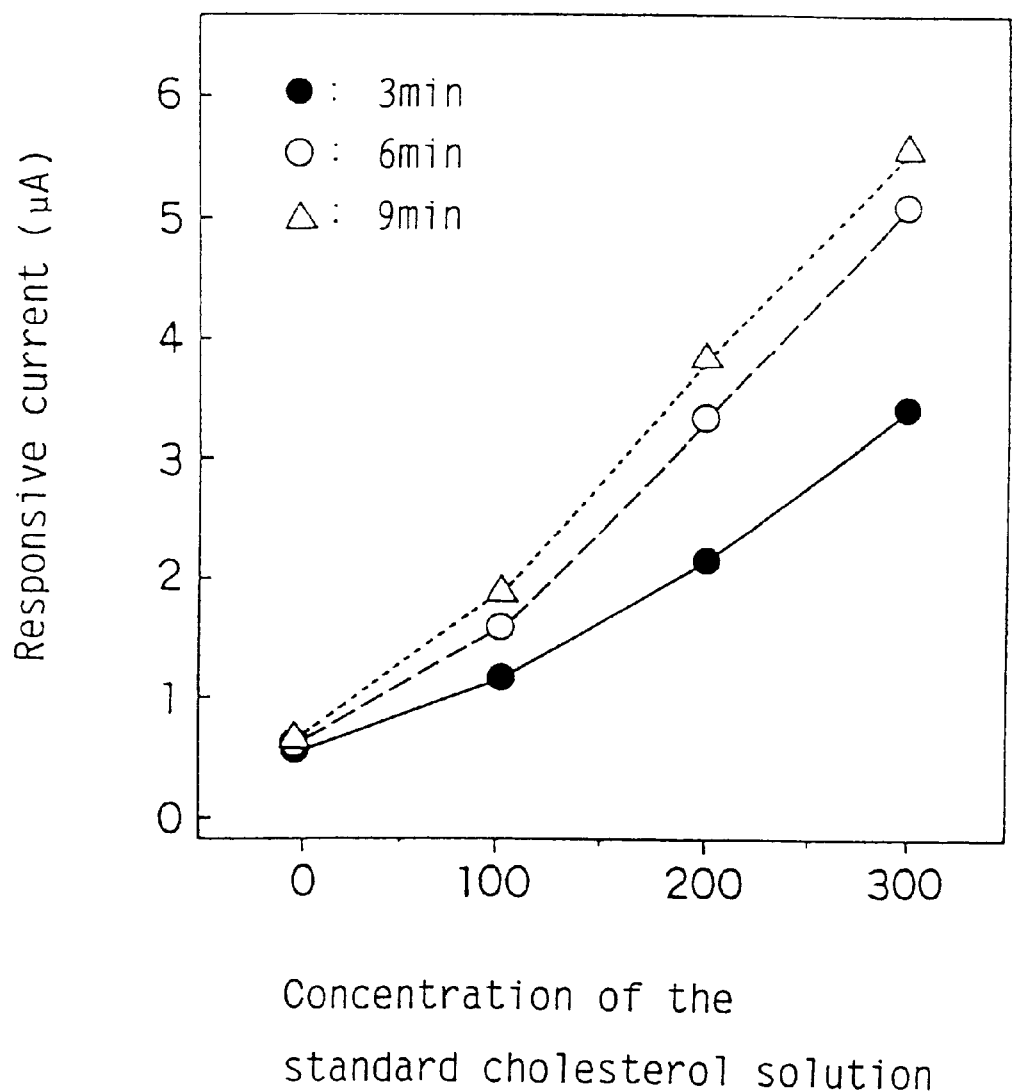
FIG. 6 is a graph showing response characteristics of a cholesterol sensor in accordance with one example of the present invention.

The cholesterol sensor thus produced was supplied with 3 μl of standard serum or physiological saline as sample solution from the opening 13 of the sample supply path. After a lapse of 3 min, a pulse voltage of +0.5 V was applied to the measuring electrode in the anode direction using the counter electrode as reference and the current value across the measuring electrode and the counter electrode was measured after 5 sec. Similarly, a voltage was applied to the measuring electrode using the counter electrode as reference at 6 and 9 min after supply of the sample solution to the sensor and the current values across the two electrodes were measured after 5 sec. FIG. 6 shows the measurement results.

As shown in FIG. 6, since the electrode system is well protected from invasion of the surfactant, the sensor shows responsive current values close to zero (0) to physiological saline which contains no cholesterol even in the presence of surfactant in the reaction reagent layer, manifesting highly linear response characteristics.

COMPARATIVE EXAMPLE 1

In the comparative example, the CMC layer was formed above the electrode system on the base plate 1 shown in FIG. 1 by dropping 5 μl of a 0.5 wt % aqueous CMC solution and drying it in a hot drier at 50° C. for 10 min. Subsequently, a mixed aqueous solution C of ChOD and potassium ferricyanide was prepared. Then, 5 μl of the solution C was dropped on the previously formed CMC layer and dried in a hot drier at 50° C. for 10 min so as to form a ChOD-potassium ferricyanide layer. After forming a ChE layer by dropping an aqueous ChE solution above this layer, the lecithin layer 10 was formed further on the ChE layer in a similar manner to that in Example 1.

Figure 7:
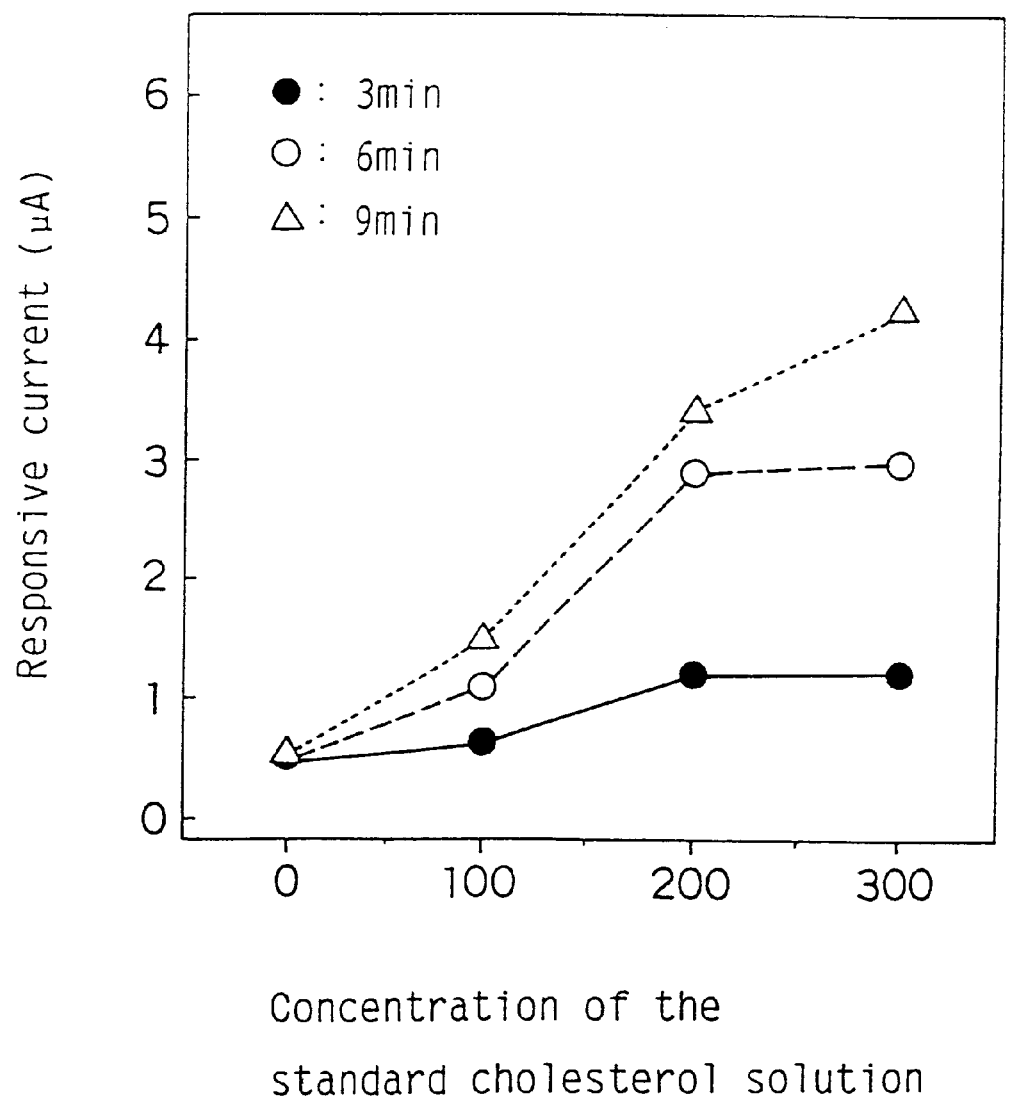
FIG. 7 is a graph showing response characteristics of a cholesterol sensor of a comparative example.

A cholesterol sensor of Comparative Example 1 was completed in a similar manner to that in Example 1 and responsive current values of the sensor to the cholesterol concentrations in various sample solutions were measured by varying the time lapse after sample supply until voltage application. FIG. 7 summarizes the measurement results.

As is clear from FIG. 7, due to the absence of surfactant in the reaction reagent layer, the sensor shows responsive current values close to zero (0) to physiological saline containing no cholesterol. But, it shows only low responsive current values to the standard serum due to lack of the surfactant.

COMPARATIVE EXAMPLE 2

In a similar manner to that in Comparative Example 1, the CMC layer and the ChOD-potassium ferricyanide layer were formed above the electrode system on the base plate 1 shown in FIG. 1. Then, 5 μl of the solution B used in Example 1 was dropped above the latter layer and dried so as to form the ChE-surfactant layer, which was then formed thereon with the lecithin layer 10 in a similar manner to that in Example 1.

Figure 8:
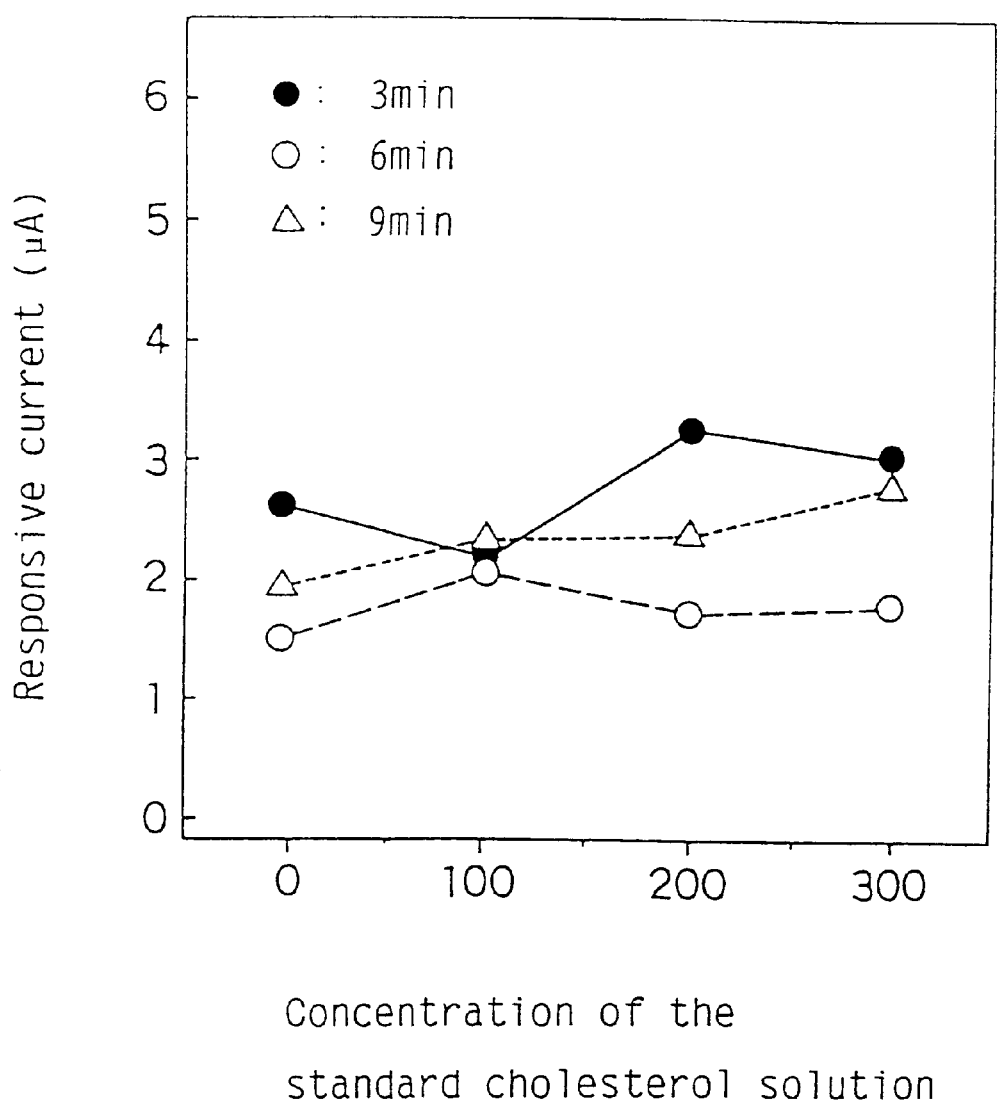
FIG. 8 is a graph showing response characteristics of a cholesterol sensor of another comparative example.

A cholesterol sensor of Comparative Example 2 was completed in a similar manner to that in Example 1 and responsive current values of the sensor to the cholesterol concentrations in various sample solutions were measured by varying the time lapse after sample supply until voltage application. FIG. 8 summarizes the measurement results.

As is evident from FIG. 8, due to the presence of surfactant in the reaction reagent layer, the sensor shows high responsive current values of 1.5 to 2.6 μA to physiological saline containing no cholesterol. To the standard serum, the sensor fails to show responsive current values dependent on the total cholesterol concentration.

EXAMPLE 2

In this example, the CMC layer and the ChOD-potassium ferricyanide-CMC layer were formed on the electrode system in a similar manner to that in Example 1. Subsequently, a mixed aqueous solution of Pseudomonas sp.-derived ChE and a surfactant Triton X-100 was dropped on an exposed side of the cover member to the sample supply path and which was formed by a combination of the spacer 11 and the cover member and dried so as to form the ChE-surfactant layer above those two layers. Positioning of the ChE-surfactant layer apart from the electrode system so as to avoid their direct mutual contact is effective to further alleviate the effect of the surfactant on the electrode system.

After forming the reaction reagent layer in this way, the cover 12 and the spacer 11 were bonded in a positional relationship shown by the dotted chain line in FIG. 1 in the same manner as in Example 1. This completed a cholesterol sensor having the structure of FIG. 3.

The cholesterol sensor thus produced showed linear responses to the total cholesterol concentration of the standard serum.

EXAMPLE 3

In this example, 5 µl of a mixed aqueous solution of CMC and sucrose was dropped on the electrode system similar to Example 1 and dried in a hot drier at 50° C. for 10 min so as to form a CMC-sucrose layer. This mixed aqueous solution contained 0.5 wt % CMC and 5 wt % sucrose. Subsequently, another mixed aqueous solution of ChOD, ChE and potassium ferricyanide was prepared and 5 µl of the solution was dropped on the CMC-sucrose layer and dried in a hot drier at 50° C. for 15 min so as to form a ChOD-ChE-potassium ferricyanide layer. An ethanol solution of n-octyl-β-D-thioglucoside (hereafter abbreviated to "Otg") was dropped so as to cover the ChOD-ChE-potassium ferricyanide layer and dried, which gave a surfactant layer. The use of an ethanol surfactant solution facilitates formation of the surfactant layer without accompanying dissolution of the ChOD-ChE-potassium ferricyanide layer and the CMC-sucrose layer. If a sensor is configured as such, introduction of a sample solution becomes easy owing to the presence of the surfactant layer, which eliminates the need of the lecithin layer 10 unlike Example 1.

After forming the reaction reagent layer in this way, the cover 12 and the spacer 11 were bonded in a positional relationship shown by the dotted chain line in FIG. 1 in the same manner as in Example 1. This completed a cholesterol sensor of Example 3.

The cholesterol sensor thus produced showed linear responses to the total cholesterol concentration of the standard serum. The response to physiological saline containing no cholesterol was apparently low, compared to that of the sensor having an equivalent amount of CMC in the hydrophilic polymer layer but containing no sucrose.

EXAMPLE 4

In this example, the CMC layer was formed on the electrode system in the same manner as in Example 1. Then, a mixed aqueous solution of ChOD, potassium ferricyanide and an oligosaccharide trehalose was dropped above the CMC layer so as to cover it and dried, which gave a ChOD-potassium ferricyanide-trehalose layer. As such, addition of a saccharide to the enzyme and electron acceptor layer gives the layer a smooth and flat surface, which effectively prevents migration of air bubbles during introduction of a sample solution. Then, a mixed aqueous solution of ChE and a surfactant Triton X-100 was dropped on an exposed side of the cover member to the sample supply path which was formed by a combination of the spacer 11 and the cover 12 and dried. In this way, the ChE-surfactant layer was formed. Such configuration where a saccharide is further contained in the reaction reagent layer formed at the electrode system side and the ChE-surfactant layer is positioned apart from the electrode system so as to avoid their direct mutual contact is effective to further alleviate the effect of the surfactant on the electrode system.

After forming the reaction reagent layer in this way, the cover 12 and the spacer 11 were bonded in a positional relationship shown by the dotted chain line in FIG. 1 in the same manner as in Example 1. This completed a cholesterol sensor of Example 4.

The cholesterol sensor thus produced showed linear responses to the total cholesterol concentration of the standard serum.

As discussed above, according to the present invention, it is possible to cause even such enzyme that requires a surfactant for expressing its enzyme activity to exert its activity effectively in a cholesterol sensor, yielding a cholesterol sensor permitting measurement in a shorter time. This cholesterol sensor is of high value and proves useful in measuring blood cholesterol levels.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A cholesterol sensor comprising an electrically insulating base plate, an electrode system having a measuring electrode and a counter electrode on said base plate, an electrode coating layer covering said electrode system and a reaction reagent layer on said electrode coating layer, said electrode coating layer covering 0.4 to 2.5 mg/cm$^2$ per unit area of said electrode system, wherein said reaction reagent layer comprises at least an enzyme for catalyzing cholesterol oxidation, an enzyme having a cholesterol ester hydrolyzing activity and a surfactant, said electrode coating layer comprises at least one compound selected from the group consisting of water-soluble cellulose derivatives and saccharides and is contained at such concentration that imparts sufficient viscosity to a sample solution for enabling it to hinder invasion of said surfactant into said electrode system when said electrode coating layer is dissolved in said sample solution supplied to said sensor.

2. The cholesterol sensor in accordance with claim 1, wherein said enzyme having a cholesterol ester hydrolyzing activity and said surfactant are contained in said reaction reagent layer at a concentration of 1.5 to 6.0 units and $0.75 \times 10^{-2}$ to $1.0 \times 10^{-2}$ µg per sensor chip, respectively, and said electrode coating layer is formed in an amount of 40 to 250 µg per sensor chip.

3. The cholesterol sensor in accordance with claim 2, wherein said enzyme for catalyzing cholesterol oxidation is contained in said reaction reagent layer at 0.15 to 1.5 units per sensor chip.

4. The cholesterol sensor in accordance with claim 1, wherein said reaction reagent layer comprises:

a first layer directly on said electrode coating layer, said first layer comprising an enzyme for catalyzing cholesterol oxidation and a water-soluble cellulose derivative or a saccharide, and a second layer above said first layer, said second layer comprising an enzyme having a cholesterol ester hydrolyzing activity and a surfactant.

5. The cholesterol sensor in accordance with claim 1, wherein said sensor further includes a cover member and a sample supply path and wherein said reaction reagent layer comprises:

a first layer directly on said electrode coating layer, said first layer comprising an enzyme for catalyzing cholesterol oxidation and a water-soluble cellulose derivative or a saccharide, and a second layer on an exposed side of said cover member to said sample supply path, said second layer comprising an enzyme having a cholesterol ester hydrolyzing activity and a surfactant.

6. The cholesterol sensor in accordance with claim 1, wherein said enzyme for catalyzing cholesterol oxidation is cholesterol oxidase or cholesterol dehydrogenase.

7. The cholesterol sensor in accordance with claim 1, wherein said reaction reagent layer further comprises an electron acceptor.

8. The cholesterol sensor in accordance with claim 1, wherein said enzyme having a cholesterol ester hydrolyzing activity is cholesterol esterase.

9. The cholesterol sensor in accordance with claim 1, wherein said electrode coating layer covers 0.8 to 1.6 mg/cm$^2$ per unit area of said electrode system.

10. The cholesterol sensor in accordance with claim 1, wherein said electrode system is made of carbon.

11. The cholesterol sensor in accordance with claim 1, wherein said electrode system comprises an underlying silver layer and a carbon layer formed above said silver layer.

12. A cholesterol sensor comprising an electrically insulating base plate, an electrode system having a measuring electrode and a counter electrode on said base plate, an electrode coating layer covering said electrode system, a cover member which is integrated to said base plate so as to form a sample supply path for supplying a sample solution to said electrode system between said cover member and said base plate, and a reaction reagent layer located on said cover member in said sample path, said electrode coating layer covering 0.4 to 2.5 mg/cm$^2$ per unit area of said electrode system, wherein said reaction layer comprises at least an enzyme for catalyzing cholesterol oxidation, an enzyme having a cholesterol ester hydrolyzing activity and a surfactant, and said electrode coating layer comprises at least one compound selected from the group consisting of water-soluble cellulose derivatives and saccharides and is contained at such concentration that imparts sufficient viscosity to a sample solution for enabling it to hinder invasion of said surfactant into said electrode system when said electrode coating layer is dissolved in said sample solution supplied to said sensor.

* * * * *